US006177611B1

(12) United States Patent
Rice

(10) Patent No.: US 6,177,611 B1
(45) Date of Patent: Jan. 23, 2001

(54) MAIZE PROMOTERS

(75) Inventor: Douglas A. Rice, Des Moines, IA (US)

(73) Assignee: Pioneer Hi-Bred International, Inc., Des Moines, IA (US)

( * ) Notice: Under 35 U.S.C. 154(b), the term of this patent shall be extended for 0 days.

(21) Appl. No.: 09/257,584

(22) Filed: Feb. 25, 1999

Related U.S. Application Data

(60) Provisional application No. 60/076,075, filed on Feb. 26, 1998.

(51) Int. Cl.[7] .............................. C12N 5/04; C12N 15/29; C12N 15/82; A01H 5/00; A01H 5/10

(52) U.S. Cl. ....................... 800/278; 435/320.1; 435/419; 435/412; 435/468; 536/24.1; 800/287; 800/298; 800/320; 800/320.1; 800/317

(58) Field of Search .................................... 435/410, 412, 435/419, 468, 69.1, 320.1; 536/23.6, 24.1; 800/278, 295, 298, 320, 320.1, 317

(56) References Cited

U.S. PATENT DOCUMENTS

| 5,466,785 | 11/1995 | De Framond ...................... 536/24.1 |
| 5,635,618 | 6/1997 | Capellades et al. ................ 536/24.1 |
| 5,639,952 | 6/1997 | Quail et al. ......................... 800/287 |

FOREIGN PATENT DOCUMENTS

| 7751/94 | 5/1995 | (AU) | .............................. C12N/15/62 |
| 77751/94 | 5/1995 | (AU) | .............................. C12N/15/62 |
| 0 342 926 A2 | 5/1989 | (EP) | .............................. C12N/15/00 |
| 0 342 926 A3 | 5/1989 | (EP) | .............................. C12N/15/00 |
| 0 353 908 A2 | 7/1989 | (EP) | .............................. C12N/15/29 |
| 0342 926 B1 | 11/1989 | (EP) | .............................. C12N/15/29 |
| 0 353908 | 2/1990 | (EP) | .............................. C12N/15/29 |
| 0 452 269 A2 | 4/1991 | (EP) | .............................. C12N/15/82 |
| 0 652 286 A1 | 11/1994 | (EP) | .............................. C12N/15/82 |
| 0652 286 A1 | 5/1995 | (EP) | .............................. C12N/15/82 |
| WO 90/02172 A1 | 3/1990 | (WO) | .............................. C12N/5/00 |
| WO 95/35386 | 12/1995 | (WO) | .............................. C12N/15/82 |
| WO 95/35386 A1 | 12/1995 | (WO) | .............................. C12N/15/82 |
| WO 94/07746 A1 | 3/1996 | (WO) | .............................. C12N/15/82 |
| WO 96/07746 A1 | 3/1996 | (WO) | .............................. C12N/15/82 |
| WO 97/05260 | 3/1996 | (WO) | .............................. C12N/15/82 |
| WO 97/05260 A2 | 2/1997 | (WO) | .............................. C12N/15/82 |

OTHER PUBLICATIONS

Uribe et al, Plant Mol. Biol., vol. 37, pp. 1069–1078, 1998.*
Kim et al, Plant Mol. Biol., vol. 24, pp. 105–117, 1994.*
Yamamoto et al, Plant Cell Physiol., vol. 35, pp. 773–778, 1994.*
Ishida et al, Nature Biotech., vol. 14, pp. 745–750, 1996.*
Horsch et al, Science, vol. 227, pp. 1229–1231, 1985.*
Montoliu et al., "A Tandem of α–tubulin Genes Preferentially Expressed inRadicular Tissues from Zea Mays," *Plant Molecular Biology*, 1989, pp. 1–15, vol. 14, Kluwer Academic Publishers, Belgium.
Joanin et al., "Nucleotide Sequence and Expression of Two cDNA Coding for TwoHistone H2B Variants of Maize," *Plant Molecular Biology*, 1992, pp. 581–588, vol. 20, Kluwer Academic Publishers, Belgium.
Berberich et al., "Molecular Cloning, Characterization and Expression of an Elongation Factor 1α Gene In Maize," *Plant Molecular Biology*, 1995, pp. 611–615, vol. 29, Kluwer Academic Publishers, Belgium.
Blast Search of H2B histone vs. SwissProt, GenBank, Dbest, and Patents Databases.
Blast Search of alpha–tubulin 3–18 vs. SwissProt, GenBank, Dbest, and Patents Databases.
Blast Search of efla–11 vs. SwissProt, GenBank, Dbest, and Patents Databases.
Blast Search of efla–15 vs. SwissProt, GenBank, Dbest, and Patents Databases.
Blast Search of efla–16 vs. SwissProt, GenBank, Dbest, and Patents Databases.
Blast Search of rps8 vs. SwissProt, GenBank, Dbest, and Patents Databases.
Blast Search of cab–10 vs. SwissProt, GenBank, Dbest, and Patents Databases.
Blast Search of cab–20 vs. SwissProt, GenBank, Dbest, and Patents Databases.
GenBank Report, Accession No. X69960, Jonin, P., Direct Submission, Submitted Jan. 7, 1993; Joanin, et al., "Molecular Cloning and Sequence Analysis of Two Genes Encoding Two Histone H2B Variants of Maize," 1994, *Physiol. Veg.*, vol. 32, pp. 693–696, Sequence from Blast Search for H2Bhistone.
GenBank Report, Accession No. X69961, Joanin, P., Direct Submission, Submitted Jan. 7, 1993; Joanin, et al., "Molecular Cloning and Sequence Analysis of Two Genes Encoding TwoHistone H2B Variants of Maize," 1994, *Physiol. Veg.*, vol. 32, pp. 693–696; Sequence from Blast Search for H2Bhistone.

(List continued on next page.)

*Primary Examiner*—Paula K. Hutzell
*Assistant Examiner*—Ashwin D. Mehta
(74) *Attorney, Agent, or Firm*—Alston & Bird LLP

(57) ABSTRACT

The present invention provides compositions and methods for regulating expression of heterologous nucleotide sequences in a plant. Compositions are novel nucleotide sequences for constitutive promoters isolated from maize genes encoding histone H2B, metallothionein, alpha-tubulin 3, elongation factor efla, ribosomal protein rps8, chlorophyll a/b binding protein, and glyceraldehyde-3-phosphate dehydrogenase. A method for constitutively expressing a heterologous nucleotide sequence in a plant using the promoter sequences disclosed herein is provided. The method comprises transforming a plant cell to comprise a heterologous nucleotide sequence operably linked to one of the constitutive promoters of the present invention and regenerating a stably transformed plant from the transformed plant cell.

31 Claims, 1 Drawing Sheet

OTHER PUBLICATIONS

GenBank Report, Accession No. S57628, deFramond, A. J., "A Metallothionein–like Gene from Maize (*Zea Mays*). Cloning and Characterization," *FEBS Lett.,* 1991, vol. 290 (1–2), pp. 103–106; Sequence from Blast Search for metallothionein.

GenBank Report, Accession No. X15704; Puigdomenech, P., Direct Submission, Submitted Jun. 29, 1989; Montoliu, et al., "A Tandem of Alpha–tubulin Genes Preferentially Expressed inRadicular Tissues from *Zea mays,*" *Plant Mol. Biol,* 1990, vol. 14(1), pp. 1–15; Puigdomenech, P., Direct Submission, Submitted Dec. 15, 1994; Sequence from Blast Search for alphatublin 3–18.

GenBank Report, Accession No. X14794; Sullivan, D. T., Direct Submission, Submitted Jul. 13, 1989; Sullivan et al., "Isolation and Characterization of a Maize Chlorophyll a/b Binding Protein Gene that Produces High Levels of mRNA in the Dark," *Mol. Gen. Genet.,* 1989, vol. 215(3), pp. 431–440; Sequence from Blast Search for cab–10 and cab–20.

GenBank Report, Accession No. X63205 and S39565; Ray, J. A., Direct Submission, Submitted Nov. 13, 1991; Knight et al., "Isolation of a Gene from Maize Encoding a Chlorophyll a/b–binding Protein,"*Plant Mol. Biol.,* 1992, vol. 19 (3), pp. 533–536; relevant for cab–10 and cab–20.

GenBank Report, Accession No. X53398 and S45324;Viret, J. F., Direct Submission, Submitted Jun. 11, 1990; Becker, et al., "The cab–m7 Gene: A Light–inducible, Mesophyll–Specific Gene of Maize," *Plant Mol. Biol.,* vol. 20(1), pp. 49–60; relevant for cab–10 and cab–20.

Kyozuka et al., Anaerobic Induction and Tissue–Specific Expression of Maize Adh1 Promoter inTransgenci Rice Plants and Their Progeny, Mol. Gen. Genet, 1991, pp. 40–48, vol. 228, MGG©Springer–Veriag , Japan.

Joanin, Nucleotide Sequence and Expression of Two cDNA Coding for TwoHistone H2B Variants of Maize, Plant Molecular Biology, 1992, pp. 581–588, vol. 20, ©1992Kluwer Academic Publisher, Belgium.

Brignon et al., Constitutive and Cell–Division–Inducible Protein–DNA Interactions in Two MaizeHistone Gene Promoters, The Plant Journal, 1993, pp. 445–457, vol. 4(3), Cedex, France.

Brignon et al., Nuclease Sensitivity and Functional Analysis of a MaizeHistone H3 Gene Promoter, Plant Molecular Biology, 1993, pp. 1007–1015, vol. 22,Kluwer Academic Publishers, Belgium.

Joanin et al., Molecular Cloning and Sequence Analysis of Two Genes Encoding TwoHistone H2B Variants of Maize, Plant Physiol. Biochem., 1994, pp. 693–696, vol. 32(5), Gauthier–villars, Cedex, France.

Manjunath et al., Molecular Characterization and Promoter Analysis of the Maize CytosolicGlyceraldehyde 3–PhosphateDehydrogenase Gene Family and its Expression During Anoxia Plant Molecular Biology, 1997, pp. 97–112, vol. 33, Kluwer Academic Publishers, Belgium.

Markmann–Mulisch et al, Nucleotide Sequence and Linkage Map Position of the Genes for Ribosomal Proteins L14 and S8 in the maize chloroplast Genome, *Eur. J. Biochem,* 1988, pp. 507–514, vol. 170.

Becker et al., The cab–m7 Gene: A Light–Inducible, Mesophyll–Specific Gene of Maize, *Plant Molecular Biology,* 1992, pp. 49–60, vol. 20, Kluwer Academic Publishers, Belgium.

* cited by examiner

MAIZE PROMOTERS

CROSS-REFERENCE TO RELATED APPLICATION

This application claims the benefit of U.S. Provisional Application Ser. No. 60/076,075, filed Feb. 26, 1998, herein incorporated by reference.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Thus, where continuous expression is desired throughout the cells of a plant, constitutive promoters are utilized. In contrast, where gene expression in response to a stimulus is desired, inducible promoters are the regulatory element of choice. In either case, additional regulatory sequences upstream and/or downstream from the core promoter sequence may be included in expression constructs of transformation vectors to bring about varying levels of constitutive or inducible expression of heterologous nucleotide sequences in a transgenic plant.

Frequently it is desirable to have constitutive expression of a DNA sequence throughout the cells of an organism. For example, increased resistance of a plant to infection by soil- and air-borne pathogens might be accomplished by genetic manipulation of the plant's genome to comprise a constitutive promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive promoter operably linked to an antisense nucleotide sequence, such that constitutive expression of the antisense sequence produces an RNA transcript that interferes with translation of the mRNA of the native DNA sequence.

Thus, isolation and characterization of constitutive promoters that can serve as regulatory regions for constitutive expression of heterologous nucleotide sequences of interest are needed for genetic manipulation of plants to exhibit specific phenotypic traits.

SUMMARY OF THE INVENTION

Compositions and methods for regulating expression of heterologous nucleotide sequences in a plant are provided. Compositions are novel nucleotide sequences for constitutive plant promoters, more particularly promoters isolated from maize genes encoding histone H2B, metallothionein, alpha-tubulin 3, elongation factor efla, ribosomal protein rps8, chlorophyll a/b binding protein, and glyceraldehyde-3-phosphate dehydrogenase. A method for constitutively expressing a heterologous nucleotide sequence in a plant using the promoter sequences disclosed herein is provided. The method comprises transforming a plant cell with a transformation vector that comprises a heterologous nucleotide sequence operably linked to one of the plant promoters of the present invention and regenerating a stably transformed plant from the transformed plant cell.

DETAILED DESCRIPTION OF THE INVENTION

Figure 1:
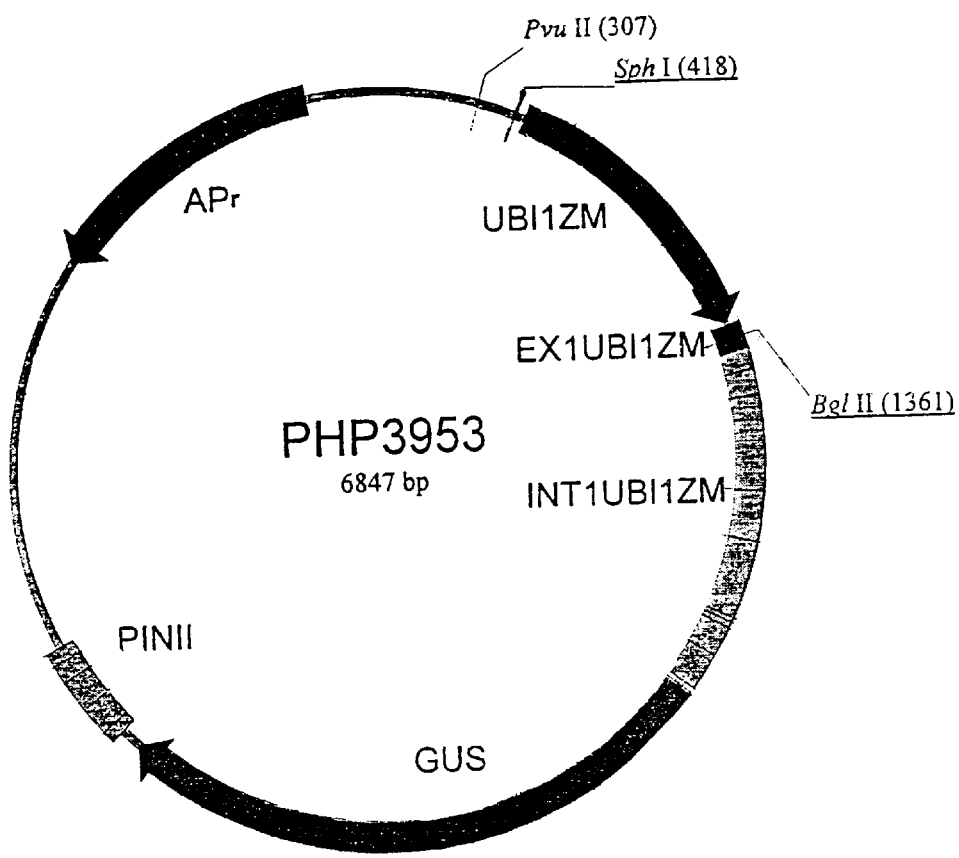
FIG. 1 shows the plasmid vector PHP3953 comprising the GUS gene operably linked to the ubiquitin promoter. Promoter fragments of the present invention were recloned into this plasmid in place of the ubiquitin promoter, and the resulting plasmid DNA was available for use in transformation studies to test for promoter activity.

Compositions of the present invention are nucleic acid molecules comprising novel nucleotide sequences for plant promoters, more particularly constitutive promoters for the maize genes encoding histone H2B; metallothionein-1; alpha-tubulin 3-18; elongation factor efla-11, efla-15, and efla-16; ribosomal protein rps8; chlorophyll a/b binding protein cab-10 and cab-20; and glyceraldehyde-3-phosphate dehydrogenase gpc4. The nucleotide sequences for these promoters are set forth in SEQ ID NOs: 1–10, respectively. In particular, the present invention provides for isolated nucleic acid molecules comprising nucleotide sequences encoding the DNA sequences deposited in a bacterial host as ATCC Accession Nos. 207123, 207120, 207125, 207121, 207122, 207124, 207126, 207127, 207128, and 207119, and variants and fragments thereof. The promoters for these maize genes were isolated from the 5' untranslated region flanking their respective transcription initiation sites. Methods for isolation of promoter regions are well known in the art. The specific method used to obtain the promoters of the present invention is described in Example 1 below.

Plasmids containing the promoter nucleotide sequences of the invention were deposited with American Type Culture Collection (ATCC), Manassas, Virginia, and assigned Accession Nos. 207123, 207120, 207125, 207121,207122, 207124, 207126, 207127, 207128, and 207119. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

By "promoter" is intended a regulatory region of DNA usually comprising a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus the promoter regions disclosed herein may further comprise upstream regulatory elements that confer tissue-specific expression of any heterologous nucleotide sequence operably linked to one of the disclosed promoter sequences. See particularly Australian Patent No. AU-A-77751/94 and U.S. Pat. Nos. 5,466,785 and 5,635,618.

The maize promoter sequences of the present invention, when assembled within a DNA construct such that the promoter is operably linked to a heterologous nucleotide sequence of interest, enable constitutive expression of the heterologous nucleotide sequence in the cells of a plant stably transformed with this DNA construct. By "heterologous nucleotide sequence" is intended a sequence that is not naturally occurring with the promoter sequence. While this nucleotide sequence is heterologous to the promoter sequence, it may be homologous or native or heterologous or foreign to the plant host. By "constitutive" is intended expression in the cells throughout a plant at most times and in most tissues.

The isolated promoter sequences of the present invention can be classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

The nucleotide sequences for the constitutive promoters of the present invention may be the naturally occurring sequences or any sequence having substantial homology. By "substantial homology" is intended a sequence exhibiting substantial functional and structural equivalence with the native or naturally occurring sequence. Any functional or structural differences between substantially homologous sequences do not effect the ability of the sequence to function as a promoter as disclosed in the present invention. Thus, any sequence having substantial sequence homology with the sequence of a particular constitutive promoter of the present invention will direct constitutive expression of an operably linked heterologous nucleotide sequence. Two promoter nucleotide sequences are considered substantially homologous when they have at least about 50%, 60%, to 70%, generally about 80%, preferably about 85%, 90%, up to 98% sequence homology.

Substantially homologous sequences of the present invention include variants of the disclosed sequences, such as those that result from site-directed mutagenesis, as well as synthetically derived sequences. Methods for mutagenesis and nucleotide sequence alterations are well known in the art. See, for example, Kunkel (1985) *Proc. Natl. Acad. Sci. USA* 82:488–492; Kunkel et al. (1987) *Methods Enzymol.* 154:367–382; U.S. Pat. No. 4,873,192; Walker et al., eds. (1983) *Techniques in Molecular Biology* (MacMillan Publishing Company, New York) and the references cited therein. Thus, the promoter nucleotide sequences of the invention include both the naturally occurring sequences as well as mutant and synthetically derived forms. Generally, nucleotide sequence variants of the invention will have at least about 50%, 60%, to 70%, generally about 80%, preferably about 85%, 90%, up to 98% sequence identity to its respective native nucleotide sequence.

Fragments of the promoter nucleotide sequences disclosed herein are also encompassed by the present invention. By "fragment" is intended a portion of the promoter nucleotide sequence. Fragments of a promoter nucleotide sequence may retain their biological activity. Thus, for example, less than the entire promoter sequences disclosed herein may be utilized to drive expression of an operably linked nucleotide sequence of interest, such as a nucleotide sequence encoding a heterologous protein. It is within skill in the art to determine whether such fragments decrease expression levels or alter the nature of expression, i.e., constitutive expression. Alternatively, fragments of a promoter nucleotide sequence that are useful as hybridization probes generally do not retain this biological activity. Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800, 900, 1,000, 1,100, 1,200, 1,300, 1,400, 1,500, 1,600, or 1,700 nucleotides, or up to the number of nucleotides present in a full-length promoter nucleotide sequence disclosed herein (i.e., 1392, 1300, 166, 1023, 1022, 1769, 461, 467, 467, and 565 for SEQ ID NOs: 1–10, respectively). Generally, fragments of a promoter sequence that retain their biological activity comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are encompassed by the compositions of the present invention.

The disclosed promoter nucleotide sequences can be used to isolate homologous promoter sequences in other plant species. Methods are readily available in the art for the hybridization of nucleic acid sequences. Promoter sequences from other plants may be isolated according to well-known techniques based on their sequence homology to the promoter sequences set forth herein. In these techniques all or part of the known nucleotide sequence is used as a probe which selectively hybridizes to other promoter nucleotide sequences present in a population of cloned genomic DNA fragments or cDNA fragments (i.e., genomic or cDNA libraries) from a chosen organism.

To obtain other homologous promoter sequences, the entire promoter nucleotide sequence or portions thereof may be used as probes capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes may be used to amplify the promoter sequences of interest from a chosen organism by the well-known process of polymerase chain reaction (PCR). This technique may be used to isolate additional promoter sequences from a desired organism or as a diagnostic assay to determine the presence of promoter sequences in an organism.

Such techniques include hybridization screening of plated DNA libraries (either plaques or colonies; see, e.g., Sambrook et al. (1989) *Molecular Cloning: A Laboratory Manual* (2d ed., Cold Spring Harbor Laboratory Press, Plainview, N.Y.) and amplification by PCR using oligonucleotide primers (see, e.g., Innis et al, eds. (1990) *PCR Protocols, a Guide to Methods and Applications,* Academic Press, New York).

For example, hybridization of such sequences may be carried out under conditions of reduced stringency, medium stringency, or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively) to DNA for the promoter sequences disclosed herein in a standard hybridization assay. See Sambrook et al. (1989) *Molecular Cloning. A Laboratory Manual* (2d ed., Cold Spring Harbor Laboratory Press, Plainview, N.Y.). In general, homologous sequences that are promoter sequences and hybridize to the promoter sequences disclosed herein will be at least 40% to 50% homologous, 60% to 70% homologous, and even 80%, 85%, 90%, 95% homologous or more with the disclosed sequence. That is, the sequence similarity of sequences may range, sharing at least about 40%, 50%, about 60%, 70%, and even about 80%, 85%, 90%, 95%, 98% sequence similarity.

The following terms are used to describe the sequence relationships between two or more nucleic acids: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis.; the CLUSTAL program is well described by Higgins et al. (1988) *Gene* 73:237–244 (1988); Higgins et al. (1989) *CABIOS* 5:151–153; Corpet et al. (1988) *Nuc. Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J Mol. Biol.* 215:403–410). Alignment is also often performed by inspection and manual alignment.

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C.

The nucleotide sequences for the constitutive promoters disclosed in the present invention, as well as variants and fragments thereof, are useful in the genetic manipulation of any plant when assembled within a DNA construct such that the promoter sequence is operably linked with a heterologous nucleotide sequence whose constitutive expression is to be controlled to achieve a desired phenotypic response. By "operably linked" is intended the transcription or translation of the heterologous nucleotide sequence is under the influence of the promoter sequence. In this manner, the nucleotide sequences for the promoters of the invention are provided in expression cassettes along with heterologous nucleotide sequences for expression in the plant of interest. It is recognized that the promoter sequences of the invention may also be used with their native coding sequences to increase or decrease expression of the native coding sequence, thereby resulting in a change in phenotype in the transformed plant.

Such expression cassettes will comprise a transcriptional initiation region comprising one of the promoter nucleotide sequences of the present invention, or variants or fragments thereof, operably linked to the heterologous nucleotide sequence whose expression is to be controlled by the constitutive promoters disclosed herein. Such an expression cassette is provided with a plurality of restriction sites for insertion of the nucleotide sequence to be under the transcriptional regulation of the regulatory regions. The expression cassette may additionally contain selectable marker genes.

In order to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

The transcriptional cassette will include in the 5'-to-3' direction of transcription, a transcriptional and translational initiation region, a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens,* such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nuc. Acids Res.* 17:7891–7903; Joshi et al. (1987) *Nuc. Acid Res.* 15:9627–9639.

The expression cassette comprising the promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the promoter sequence of the present invention and any additional nucleotide sequence(s) may be optimized for increased expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831 and 5,436,391, and Murray et al. (1989) *Nuc. Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak and Sarnow (1991) *Nature* 353:90–94); untranslated leader from the coat protein mRNA of alfalfa mosaic virus (AMV RNA 4) (Jobling and Gehrke (1987) *Nature* 325:622–625); tobacco mosaic virus leader (TMV) (Gallie et al. (1989) *Molecular Biology of RNA,* pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In those instances where it is desirable to have the constitutively expressed product of the heterologous nucleotide sequence directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The expression cassette comprising the particular promoter sequence of the present invention operably linked to a heterologous nucleotide sequence of interest can be used to transform any plant. In this manner, genetically modified plants, plant cells, plant tissue, seed, and the like can be obtained. Transformation protocols may vary depending on the type of plant or plant cell, i.e., monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad Sci. USA* 83:5602–5606), Agrobacterium-mediated transformation (Hinchee et al. (1988) *Biotechnology* 6:915–921), direct gene transfer (Paszkowski et al. (1984) *EMBO J* 3:2717–2722), and ballistic particle acceleration (see, for example, Sanford et al. U.S. Pat. No. 4,945,050; Tomes et al. (1995) in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et aL (1987)

*Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Klein et al. (1988) *Plant Physiol.* 91:440–444 (maize); From et al. (1990) *Biotechnology* 8:833–839; Hooydaas-Van Slogteren and Hooykaas (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. G. P. Chapman et al. (Longman, New York), pp. 197–209 (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The promoter nucleotide sequences and methods disclosed herein are useful in regulating constitutive expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. patent application Ser. Nos. 08/838,763 (U.S. Pat. No. 5,900,389), filed Apr. 10, 1997; 08/824,379 (U.S. Pat. No. 5,885,80116), filed Mar. 26, 1997; 08/824,382 (U.S. Pat. No. 5,885,802), filed Mar. 26, 1997; and U.S. Pat. No. 5,703,409; herein incorporated by reference. Another example is lysine and/or sulfur rich seed protein encoded by the soybean 2S albumin described in U.S. Ser. No. 08/618,911, U.S. Pat. No. 5,850,016, filed Mar. 20, 1996, and the chymotrypsin inhibitor from barley, Williamson et al. (1987) *Eur. J Biochem.* 165:99–106, the disclosures of which are herein incorporated by reference.

Derivatives of the coding sequences can be made by site directed mutagenesis to increase the level of preselected amino acids in the encoded polypeptide. For example, the gene encoding the barley high lysine polypeptide (BHL) is derived from barley chymotrypsin inhibitor, U.S. Ser. No. 08/740,682 (pending), filed Nov. 1, 1996, and PCT/US97/20441, filed Oct. 31, 1997, the disclosures of each are incorporated herein by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference)); corn (Pedersen et al. (1986) *J Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example Bacillus thuringiensis toxic protein genes (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. patent application Ser. No. 08/484,815 (U.S. Pat. No. 5,792,931), filed Jun. 7, 1995); avirulence (avr) and disease resistance (R) genes (Jones et al. (1994) *Science* 266:789; Martin et al. (1993) *Science* 262:1432; Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Sterility genes can also be encoded in an expression cassette and provide an alternative to physical detasseling.

Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in U.S. patent application Ser. Nos. 08/838,763 (U.S. Pat. No. 5,990,389), filed Apr. 10, 1997; 08/824,379 (U.S. Pat. No. 5,885,801), filed Mar. 26, 1997; 08/824,382 (U.S. Pat. No. 5,885,802), filed Mar. 26, 1997; and U.S. Pat. No. 5,703,409 issued Dec. 30, 1997, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321 issued Feb. 11, 1997. Genes such as B-Ketothiolase, PHBase (polyhydroxyburyrate synthase) and acetoacetyl-CoA reductase (see Schubert et al. (1988) *J Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Thus, the heterologous nucleotide sequence operably linked to one of the constitutive promoters disclosed herein may be a structural gene encoding a protein of interest. Examples of such heterologous genes include, but are not limited to, genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. More particularly, the constitutive promoters disclosed herein and identified as weak constitutive promoters are useful in transforming plants to constitutively express an avirulence gene as disclosed in the copending applications both entitled "*Methods for Enhancing Disease Resistance in Plants,*" U.S. patent application Ser. No. 60/075,151, filed Feb. 26, 1998, and U.S. patent application Ser. No. 60/092,464, filed Jul. 11, 1998, both of which are herein incorporated by reference. Such weak promoters may cause activation of the plant defense system short of hypersensitive cell death. Thus, there is an activation of the plant defense system at levels sufficient to protect from pathogen invasion. In this state, there is at least a partial activation of the plant defense system wherein the plant produces increased levels of antipathogenic factors such as PR proteins, i.e., PR-1, cattiness, a-glucanases, etc.; secondary metabolites; phytoalexins; reactive oxygen species; and the like.

Alternatively, the heterologous nucleotide sequence operably linked to one of the constitutive promoters disclosed herein may be an antisense sequence for a targeted gene. By "antisense DNA nucleotide sequence" is intended a sequence that is in inverse orientation to the 5' to 3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequences disclosed herein may be operably linked to antisense DNA sequences to reduce or inhibit expression of a native protein in the plant.

The following examples are offered by way of illustration and not by way of limitation.

EXPERIMENTAL

Promoter regions for maize genes encoding histone H2B, metallothionein, alpha-tubulin 3-18, elongation factor efla (efla-11, efla-15, and efla-16), ribosomal protein rps8, chlorophyll a/b binding protein (cab-10 and cab-20), and glyceraldehyde-3-phosphate gpc4 were isolated from maize plants and cloned. These genes were selected as sources of constitutive promoters based on the developmental and spatial expression of their gene products. The method for their isolation is described below.

Histones are classified on the basis of their role in chromatin structure. The histone H2B is one of four histones contributing to the nucleosome core. Of the core histones H2A, H2B, H3, and H4, H2B is the least conserved from one species to another. In maize, it exists in the form of multiple variants encoded by a large multigenic family. The maize H2B histones are constitutively expressed at a high level in meristematic tissues throughout the plant. The novel promoter sequence for a maize gene encoding one of these H2B histones is set forth in SEQ ID NO: 1.

Metallothioneins make up a class of proteins that are constitutively expressed in low copy number in cells throughout a plant. Expression of these proteins in mammalian cells is inducible in response to stress and to elevated concentrations of trace elements and hormones. The novel promoter sequence for a maize gene encoding one of these metallothioneins, met- 1, is set forth in SEQ ID NO: 2.

Alpha-tubulins play a key role in the cytoskeleton of a plant, contributing to microtubule formation. In maize, these proteins are encoded by a family of genes. Generally, these genes are constitutively expressed in all meristematic tissues, though some are preferentially expressed in certain tissues (see Montoliu et al. (1989) *Plant Mol. BioL* 14:1–15; Montoliu et al. (1990) *Gene* 94:201–207). The novel promoter sequence for a maize gene encoding alpha-tubulin 3–18 is set forth in SEQ ID NO: 3.

Elongation factor efla is one of four subunits of the translation elongation factor 1 protein. This subunit plays a role in binding aminoacyl tRNA to the ribosome's acceptor site during protein synthesis. However, it has been found to play a number of other diverse roles in the cell, and hence is a multifunctional protein (see Durso and Cyr (1994) *Protoplasma* 180:99–105 for a review). In maize, efla is encoded by a family of genes comprising at least 6 members (see Berberich et al. (1995) *Plant Mol. Biol.* 29:611–615). Novel promoter sequences for three maize genes encoding efl a proteins, efla-11, efla-15, and efla-16, are set forth in SEQ ID NOs: 4, 5, and 6, respectively.

Ribosomal proteins contribute to the structure of ribosomes. A novel promoter sequence for a gene encoding a maize ribosomal protein rps8 is set forth in SEQ ID NO: 7.

Chlorophyll a/b binding protein is associated with photosystem II in the thylakoid membranes. Expression of this protein in leaf tissues is elevated in the light. Novel promoter sequences for two maize genes encoding maize chlorophyll a/b binding proteins, cab-10 and cab-20, are set forth in SEQ ID NOs: 8 and 9, respectively. The cab-10 promoter sequence shares homology (97% in an overlap from nt 1–271 of SEQ ID NO: 8) with a maize cab-m7 gene sequence (emb Accession No. X53398/ZMCABM7). The C-terminal end of the cab-10 promoter sequence disclosed herein is unique from nt 272–467. The cab-20 promoter sequence shares homology (98% in an overlap from nt 1–85 of SEQ ID NO:9) with this same cab-m7 gene sequence. The C-terminal end of the cab-20 promoter sequence disclosed herein is unique from nt 86–467. Fragments comprising contiguous nucleotides of the cab-10 and cab-20 promoters disclosed herein are preferably obtained from the unique C-terminal end of these promoter sequences, but fragments may overlap the N-terminal regions of homology, and thus include contiguous nucleotides within this region of overlap.

Glyceraldehyde-3-phosphate dehydrogenase is a glycolytic enzyme. A novel promoter sequence for a maize gene encoding glyceraldehyde-3-phosphate dehydrogenase gpc4 is set forth in SEQ ID NO: 10.

EXAMPLE 1

Isolation of Promoter Sequences

The procedure for promoter isolation is described in the User Manual for the GenomeWalker kit sold by Clontech Laboratories, Inc., Palo Alto, Calif. Genomic DNA from maize line A63 was extracted by grinding 10-day old seedling leaves in liquid nitrogen, and the DNA prepared as described by Chen and Dellaporta (1994) in *The Maize Handbook*, ed. Freeling and Walbot (Springer-Verlag, Berlin).

RNase A was added to 10 pg/ml and then incubated at 37° C. for 1 hr. The DNA was then extracted once with phenol-chloroform, then chloroform, then ethanol precipitated and resuspended in TE (10 mM Tris pH 8.0, 1 mM EDTA). The DNA was then used exactly as described in the GenomeWalker User Manual (Clontech PT3042-1 version PR68687). Briefly, the DNA was digested separately with restriction enzymes DraI, EcoRV, PvuII, ScaI, and StuI, all blunt end cutters. The GenomeWalker adapters were then ligated onto the ends of the restricted DNA. The resulting DNA is referred to as DL1-DL5, respectively.

For isolation of specific promoter regions, two nonoverlapping gene-specific primers (usually 27 bp in length) were designed from the sequences of abundant ESTs in the Pioneer/HGS database. The primers were designed to amplify the region upstream of the coding sequence, i.e., the 5' untranslated region and promoter region of the chosen gene. The sequences of the primers are given below for each promoter described. The first round of PCR was performed on each DNA sample (DL 1–5) with Clontech primer AP1 (sequence 5'-gtaatacgactcactatagggc-3'; SEQ ID NO: 11) and the gene-specific primer (gsp)1 with the following sequences:

histone H2B gsp1 sequence: 5'-cgcgggctcctcctccgccggcttctt-3' (SEQ ID NO: 12)
metallothionein gsp1 sequence: 5'-gtacttcttgccgcacttgcagcttga-3' (SEQ ID NO: 13)
alpha-tubulin 3 gsp1 sequence: 5'-ggtcttgtcaccgggcatctgaccatc-3' (SEQ ID NO: 14)
efla gsp1 sequence: 5'-gtcctgtggtggtcgacttgccagagt-3' (SEQ ID NO: 15)
rps8 gsp1 sequence: 5'-ttcttcctccaggccttctgctttcca-3' (SEQ ID NO: 16)
cab gsp1 sequence: 5'-aggagacgacgacggcacgttcacggc-3' (SEQ ID NO: 17)
gpc4 sequence: 5'-taatcggtgctgatgaaggggtcgttc-3' (SEQ ID NO: 18)

PCR was performed in a model PTC-100 thermal cycler with HotBonnet from MJ Research (Watertown, Mass.) using reagents supplied with the GenomeWalker kit. The following cycle parameters were used: 7 cycles of 94° C. for 2 sec, then 72° C. for 3 min, followed by 32 cycles of 94° C. for 2 sec, and 67° C. for 3 min. Finally, the samples were held at 67° C. for 4 min, then at 4° C. until further analysis.

As described in the User Manual, the DNA from the first round of PCR was then diluted and used as a template in a second round of PCR using the Clontech AP2 primer (sequence 5'-actataggggcacgcgtggt-3'; SEQ ID NO: 19) and gene-specific primer (gsp)2 with the following sequences:

histone H2B gsp2 sequence: 5'-gggcttcttctggccttgggcgccat-3' (SEQ ID NO: 20)
metallothionein gsp2 sequence: 5'agccgcagcttgatccgcagttgcaag-3' (SEQ ID NO: 21)
alpha-tubulin 3 gsp2 sequence: 5'-cccagcacgcgtttccgacctggatac-3' (SEQ ID NO: 22)
efla gsp2 sequence: 5'-tggccaataaccacaatgttgatgtg-3' (SEQ ID NO: 23)
rps8 gsp2 sequence: 5'-cgcttgtgcatcgagtcacgcgagata-3' (SEQ ID NO: 24)
cab gsp2 sequence: 5'-gaaggctgtggaggagagggccatggt-3' (SEQ ID NO: 25)
gpc4 gsp2 sequence: 5'-acccattgatcccgatcttgatct-3' (SEQ ID NO: 26)

The cycle parameters for the second round were: 5 cycles of 94° C. for 2 sec, then 72° C. for 3 min, followed by 20 cycles of 94° C. for 2 sec, and 67° C. for 3 min Finally, the samples were held at 67° C. for 4 min, and then held at 4° C. Approximately 10 μl of each reaction were run on a 0.8% agarose gel, and bands (usually 500bp or larger) were excised, purified with the Sephaglas BandPrep kit (Pharmacia, Piscataway, N.J.), and cloned into the TA vector pCR2.1 (Invitrogen, San Diego, Calif.). Clones were sequenced for verification, and then the mini-prep DNA was diluted 1:30 in water and 1 μl was amplified with gene-specific primer (gsp)3 (sequences below) and the Clontech AP2 primer with the following cycle parameters: five cycles of 94° C. for 2 sec, 46° C. for 30 sec, 72° C. for min, followed by 20 cycles of 94° C. for 2 sec, 67° C. for 3 min, then 67° C. for 4 min, and held at 4° C.

histone H2B gsp3 sequence: 5'-gaccatggtgtcgtgtggatccgatgcggctgct-3' (SEQ ID NO: 27)
metallothionein gsp3 sequence: 5'-gaccatggtgtcgtgtggatcccttgtggtgc-3' (SEQ ID NO: 28)
alpha-tubulin gsp3 sequence: 5'-gaccatggtgtcgtgtggatccggtgttgttgaacg-3' (SEQ ID NO: 29)
efla-11 and efla-15 gsp3 sequence: 5'-gaccatggtgtcgtgtggatccgtgagattgaac-3' (SEQ ID NO: 30)
efla-16 gsp3 sequence: 5'-gaccatggtgtcgtcgtgtggatccgtgaagcttaa-3' (SEQ ID NO: 31)
rps8 gsp3 sequence: 5'-gaccatggtgtcgtgtggatccgcctgctccttgtc-3' (SEQ ID NO: 32)

cab gsp3 sequence: 5'-gaccatggtgtcgtgtggatcctgcactgctac-3' (SEQ ID NO: 33)

gpc4 gsp3 sequence: 5'-gaccatggtgtcgtgtggatccacaaacacaagc-3' (SEQ ID NO: 34)

Ten μl of the resulting amplified DNA was run out on a 0.8% agarose gel, purified with Sephaglas, and cloned into the PCR2.1 TA vector. Final sequences were determined on the resulting plasmids.

EXAMPLE 2

Transient Gene Expression Data Using Promoter Sequences

A transient gene expression assay was used to test the cloned DNAs for promoter activity. The promoters were recloned into plasmid PHP3953 (FIG. 1) digested with BglII and SphI or with BglII and PvuII to remove the ubiquitin promoter. The new promoter fragments were inserted in place of the ubiquitin promoter such that the ubiquitin 5' untranslated region and intron were now between the test promoter and the GUS reporter gene.

Experiments were performed with immature embryos, essentially the scutellar surface. Immature GS3 maize embryos were isolated from ears 9–11 days after pollination using a scalpel. Prior to embryo isolation, pollinated ears were surface-sterilized with a microdetergent and 25% commercial bleach mixture, then washed with 3 exchanges of sterile $H_2O$. Isolated immature embryos (1.4–1.7 mm) were placed on bombardment medium and aligned in a target grid in preparation for bombardment.

Immature embryos were then transformed by the tungsten particle biolistic method (Tomes et al (1995) in *Plant Cell, Tissue, and Organ Culture. Funadamental Methods*, ed. Gamborg and Phillips (Springer-Verlag, Berlin); Koziel et al. (1993) *Bio/Technology* 11:194–200) using a high pressure particle delivery system (Biolistic Particle Delivery System Model PDS-100 by DuPont). Plasmid DNA comprising a promoter sequence of the invention operably linked to the GUS gene was bombarded into the maize immature embryos. Following culture for 40 hours, bombarded embryos were stained with X-Gluc staining solution (McCabe et al. (1988) *Bio/Technology* 6(87):923–926) for 12 h at 37° C. in the dark. GUS activity was then measured, using the ubiquitin promoter as a control, by counting blue spots after staining for GUS activity as described elsewhere (see Jefferson (1987) *Plant Mol. Biol. Rep.* 5:387–405). Transient expression data are shown in Table 1.

TABLE 1

Promoter activity as measured by transient expression of GUS (see Christensen and Quail (1989) Plant Mol. Biol. 12:619–632 for details of ubiquitin promoter activity).

| Gene | #Blue spots | Average |
|---|---|---|
| Ubiquitin (control) | 395, 155, 307, 416 | 318 |
| histone H2B | 2127, 2826, 2830 | 2594 |
| tub3-18 (alpha-tubulin 3) | 2542, 1832, 2727 | 2367 |
| met-1 (methallothionein) | 163, 111, 27 | 100 |
| efla-16 (elongation factor 1a) | 136, 2, 0 | 46 |
| efla-15 (another family member) | 81, 38, 25 | 48 |

Promoter activity of the promoter sequences for the alpha-tubulin and histone H2B genes was significantly stronger than that of the ubiquitin promoter, indicating these as strong constitutive promoters. Promoter activity of the promoter sequence for the metallothionein gene was considerably lower than that of the ubiquitin promoter, indicating this is a weak constitutive promoter.

EXAMPLE 3

Transformation and Regeneration of Transgenic Plants

Immature GS3 maize embryos were bombarded with a plasmid containing the promoter sequence operably linked to the GUS gene plus a plasmid containing the selectable marker gene PAT (Wohlleben et al. (1988) *Gene* 70:25–37) that confers resistance to the herbicide Bialaphos. Transformation was performed as described in Example 1. See Appendix for examples of bombardment (560Y), selection (560R), hormone-containing regeneration (288J), and hormone-free (272V) media.

One day after bombardment, the embryos were transferred from bombardment medium to selection medium containing 3 mg/liter Bialaphos and subcultured on selection medium every 2 weeks. After approximately 10 weeks of selection, selection-resistant callus clones were transferred to hormone-containing medium to initiate plant regeneration. Following somatic embryo maturation (2–4 weeks), well-developed somatic embryos were transferred to medium for germination and transferred to the lighted culture room. Approximately 7–10 days later, developing plantlets were transferred to hormone-free medium in tubes for 7–10 days until plantlets were well established. Plants were then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

Promoter activity in transformed plant tissues was assessed by measuring expression of GUS. Plant tissue samples were placed into the wells of 12-well cell culture clusters and stained with X-Gluc staining solution for 12 h at 37° C. in the dark. Samples were then scored for GUS staining. GUS staining score ranged from 0 (negative)–6 (highest). These staining scores served as a measure of level of GUS expression. Results are shown in Table 2.

Six transformation events have been evaluated for the H2B promoter. Overall, five out of six events scored strong GUS expression in maize plants, with one event scoring median expression. GUS expression was particularly strong in leaf, root, and tassel, with these tissues having GUS staining scores of 5–6 in all events. GUS expression in husk and silk was slightly lower, with these two tissues mostly having staining scores of 4–5. GUS staining with kernels was conducted with event TC7394 and it scored strong. In general, H2B is a strong promoter in maize embryos, callus, and different tissues.

Four transformation events have been evaluated for the met- 1 promoter. Overall, three events scored strong GUS expression and one event scored median expression. GUS expression was found in all plant tissues, including leaf, root, husk, silk, and tassel, with these tissues mostly having staining scores of 4–5. The expression pattern seems similar to that observed with the tub3-18 promoter.

Five transformation events have been evaluated for the tub3-1 8 promoter. Overall, three events scored strong GUS expression and two scored median expression. GUS expression was found in all plant tissues, including leaf, root, husk, silk, and tassel, with these tissues mostly having staining scores of 3–5. GUS staining with kernels was conducted with event TC7406 and it scored very strong.

Five transformation events have been evaluated the efla-15 promoter. Overall, three events scored strong GUS expression, one event scored median expression, and one event scored weak expression. GUS expression was found in all plant tissues, including leaf, root, husk, silk, and tassel, with these tissues mostly having staining scores of 3–5.

The ubiquitin promoter was used as a control. Five transformation events have been evaluated. Overall, two events scored strong GUS expression and three scored weak expression. GUS expression was found in all plant tissues, including leaf, root, husk, silk, and tassel. With those transformation events exhibiting strong expression, GUS was expressed in all different tissues, with tissues mostly having staining scores of 4–5. With those transformation events exhibiting weak expression, GUS was expressed in leaf, root, and tassel, with these tissues mostly having staining scores of 1–3. There was very little GUS expression in husk and silk tissues in those transformation events that exhibited weak expression.

TABLE 2

Gus expression as driven by various promoters of the invention.

| Promoters | Event | GUS expression | GUS PCR |
|---|---|---|---|
| H2B | TC4703 | strong | na |
|  | TC4701 | strong | na |
|  | TC4694 | strong | na |
|  | TC7392 | median | positive |
|  | TC7394 | strong | positive |
|  | TC7396 | strong | positive |
| met-1 | TC7413 | strong | positive |
|  | TC7414 | weak | positive |
|  | TC7415 | strong | positive |
|  | TC7416 | strong | positive |
| tub3-18 | TC7406 | strong | positive |
|  | TC7407 | strong | positive |
|  | TC7408 | strong | positive |
|  | TC7409 | median | positive |
|  | TC7410 | median | positive |
| efla-15 | TC7418 | median | positive |
|  | TC7419 | strong | positive |
|  | TC7420 | strong | positive |
|  | TC7421 | weak | positive |
|  | TC7422 | strong | positive |
| Ubi | TC7390 | strong | positive |
|  | TC7386 | strong | positive |
|  | TC7387 | weak | positive |
|  | TC7388 | weak | positive |
|  | TC7389 | weak | positive |

APPENDIX

272 V

| Ingredient | Amount | Unit |
|---|---|---|
| D-I H$_2$O | 950.000 | ml |
| MS Salts (GIBCO 11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:
@ = Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
## = Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.
Total Volume (L) = 1.00

288 J

| Ingredient | Amount | Unit |
|---|---|---|
| D-I H$_2$O | 950.000 | ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| .1 mM Abscisic Acid | 1.000 | ml |
| Bialaphos 1 mg/ml # | 3.000 | ml |

Directions:
@ = Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
Add 3.5 g/L of Gelrite for cell biology.
## = Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.
Total Volume (L) = 1.00

560 R

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:
@ = Add after bringing up to volume
# = Add after sterilizing and cooling to temp
Dissolve ingredients in D-I H$_2$O in sequence
Adjust to pH 5.8 with KOH
Bring up to volume with D-I H$_2$O
Sterilize and cool to room temp.
Total Volume (L) = 1.00

560 Y

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@ = Add after bringing up to volume
# = Add after sterilizing and cooling to temp.
Dissolve ingredients in D-I H$_2$O in sequence
Adjust to pH 5.8 with KOH -continued

560 Y

| Ingredient | Amount | Unit |
|---|---|---|

Bring up to volume with D-I $H_2O$
Sterilize and cool to room temp.
Autoclave less time because of increased sucrose
Total Volume (L) = 1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule having a nucleotide sequence for a promoter that is capable of initiating transcription in a plant cell, wherein said nucleotide sequence is selected from the group consisting of:
   a) a nucleotide sequence comprising the sequence set forth in SEQ ID NO: 1, 2,3,4,5,6,7, or10;
   b) a nucleotide sequence selected from the group consisting of sequences deposited as ATCC Accession Nos. 207123, 207120, 207125, 207121, 207122, 207124, 207126, and 207119;
   c) a nucleotide sequence comprising at least 40 contiguous nucleotides of the sequence set forth in SEQ ID NO: 1, 2, 3, 4, 5, 6, 7, or 10; and
   d) a nucleotide sequence that has at least about 70% sequence identity to a sequence set forth in a) or b).

2. A DNA construct comprising a nucleotide sequence of claim 1 operably linked to a heterologous nucleotide sequence of interest.

3. A vector comprising the DNA construct of claim 2.

4. a host cell having stably incorporated in its genome the DNA construct of claim 2.

5. An isolated nucleic acid molecule having a nucleotide sequence for a promoter that is capable of initiating transcription in a plant cell, wherein said nucleotide sequence is selected from the group consisting of:
   a) a nucleotide sequence comprising the sequence set forth in SEQ ID NO: 8;
   b) the nucleotide sequence deposited as ATCC Accession No. 207127;
   c) a nucleotide sequence comprising at least 40 contiguous nucleotides of the C-terminal end of the sequence set forth in SEQ ID NO: 8, wherein said C-terminal end comprises nucleotides 272–467 of SEQ ID NO: 8; and
   d) a nucleotide sequence that has at least about 70% sequence identity to a sequence set forth in a) or b).

6. A DNA construct comprising a nucleotide sequence of claim 5 operably linked to a heterologous nucleotide sequence of interest.

7. A vector comprising the DNA construct of claim 6.

8. A host cell having stably incorporated in its genome the DNA construct of claim 6.

9. An isolated nucleic acid molecule having a nucleotide sequence for a promoter that is capable of initiating transcription in a plant cell, wherein said nucleotide sequence is selected from the group consisting of:
   a) a nucleotide sequence comprising the sequence set forth in SEQ ID NO: 9;
   b) the nucleotide sequence deposited as ATCC Accession No. 207128;
   c) a nucleotide sequence comprising at least 40 contiguous nucleotides of the C-terminal end of the sequence set forth in SEQ ID NO: 9, wherein said C-terminal end comprises nucleotides 86–467 of SEQ ID NO: 9; and
   d) a nucleotide sequence that has at least about 70% sequence identity to a sequence set forth in a) or b).

10. A DNA construct comprising a nucleotide sequence of claim 9 operably linked to a heterologous nucleotide sequence of interest.

11. A vector comprising the DNA construct of claim 10.

12. A host cell having stably incorporated in its genome the DNA construct of claim 10.

13. A method for expressing a heterologous nucleotide sequence in a plant, said method comprising transforming a plant cell with a DNA construct comprising said heterologous nucleotide sequence operably linked to a promoter that is capable of initiating transcription in a plant cell and regenerating a stably transformed plant from said plant cell, wherein said promoter comprises a nucleotide sequence selected from the group consisting of:
   a) a nucleotide sequence comprising the sequence set forth in SEQ ID NO: 1, 2, 3, 4, 5, 6, 7, or 10;
   b) a nucleotide sequence selected from the group consisting of sequences deposited as ATCC Accession Nos. 297123, 207120, 207125, 207121, 207122, 207124, 207126, and 207119;
   c) a nucleotide sequence comprising at least 40 contiguous nucleotides of the sequence set forth in SEQ ID NO: 1, 2, 3, 4, 5, 6, 7, or 10; and
   d) a nucleotide sequence that has at least about 70% sequence identity to a sequence set forth in a) or b).

14. The method of claim 13, wherein said plant is a monocot.

15. The method of claim 14, wherein said monocot is maize.

16. The method of claim 13, wherein said plant is a dicot.

17. A method for expressing a heterologous nucleotide sequence in a plant, said method comprising transforming a plant cell with a DNA construct comprising said heterologous nucleotide sequence operably linked to a promoter that is capable of initiating transcription in a plant cell and regenerating a stably transformed plant from said plant cell, wherein said promoter comprises a nucleotide sequence selected from the group consisting of:
   a) a nucleotide sequence comprising the sequence set forth in SEQ ID NO: 8;
   b) the nucleotide sequence deposited as ATCC Accession No. 207127;
   c) a nucleotide sequence comprising at least 40 contiguous nucleotides of the C-terminal end of the sequence set forth in SEQ ID NO: 8, wherein said C-terminal end comprises nucleotides 272–467 of SEQ ID NO: 8; and
   d) a nucleotide sequence that has at least about 70% sequence identity to a sequence set forth in a) or b).

18. A method for expressing a heterologous nucleotide sequence in a plant, said method comprising transforming a plant cell with a DNA construct comprising said heterologous nucleotide sequence operably linked to a promoter that is capable of initiating transcription in a plant cell and regenerating a stably transformed plant from said plant cell, wherein said promoter comprises a nucleotide sequence selected from the group consisting of:
   a) a nucleotide sequence comprising the sequence set forth in SEQ ID NO: 9;
   b) the nucleotide sequence deposited as ATCC Accession No. 207128;
   c) a nucleotide sequence comprising at least 40 contiguous nucleotides of the C-terminal end of the sequence set forth in SEQ ID NO: 9, wherein said C-terminal end comprises nucleotides 86–467 of SEQ ID NO: 9; and
   d) a nucleotide sequence that has at least about 70% sequence identity to a sequence set forth in a) or b).

19. A plant cell stably transformed with a DNA construct comprising a heterologous nucleotide sequence operably linked to a promoter that is capable of initiating transcription in said plant cell, wherein said promoter comprises a nucleotide sequence selected from the group consisting of:
   a) a nucleotide sequence comprising the sequence set forth in SEQ ID NO: 1, 2, 3, 4, 5, 6, 7, or 10;
   b) a nucleotide sequence selected from the group consisting of sequences deposited as ATCC Accession Nos. 207123, 207120, 207125, 207121,207122, 207124, 207126, and 207119;
   c) a nucleotide sequence comprising at least 40 contiguous nucleotides of the sequence set forth in SEQ ID NO: 1, 2, 3, 4, 5, 6, 7, or 10; and
   d) a nucleotide sequence that has at least about 70% sequence identity to a sequence set forth in a) or b).

20. The plant cell of claim 19, wherein said plant cell is from a monocot.

21. The plant cell of claim 20, wherein said monocot in maize.

22. The plant cell of claim 19, wherein said plant cell is from a dicot.

23. A plant cell stably transformed with a DNA construct comprising a heterologous nucleotide sequence operably linked to a promoter that is capable of initiating transcription in said plant cell, wherein said promoter comprises a nucleotide sequence selected from the group consisting of:
   a) a nucleotide sequence comprising the sequence set forth in SEQ ID NO: 8;
   b) the nucleotide sequence deposited as ATCC Accession No. 207127;
   c) a nucleotide sequence comprising at least 40 contiguous nucleotides of the C-terminal end of the sequence set forth in SEQ ID NO: 8, wherein said C-terminal end comprises nucleotides 272–467 of SEQ ID NO: 8; and
   d) a nucleotide sequence that has at least about 70% sequence identity to a sequence set forth in a) or b).

24. A plant cell stably transformed with a DNA construct comprising a heterologous nucleotide sequence operably linked to a promoter that is capable of initiating transcription in said plant cell, wherein said promoter comprises a nucleotide sequence selected from the group consisting of:
   a) a nucleotide sequence comprising the sequence set forth in SEQ ID NO: 9;
   b) the nucleotide sequence deposited as ATCC Accession No. 207128;
   c) a nucleotide sequence comprising at least 40 contiguous nucleotides of the C-terminal end of the sequence set forth in SEQ ID NO: 9, wherein said C-terminal end comprises nucleotides 86–467 of SEQ ID NO: 9; and
   d) a nucleotide sequence that has at least about 70% sequence identity to a sequence set forth in a) or b).

25. A plant stably transformed with a DNA construct comprising a heterologous nucleotide sequence operably linked to a promoter that is capable of initiating transcription in a plant cell, wherein said promoter comprises a nucleotide sequence selected from the group consisting of:
   a) a nucleotide sequence comprising the sequence set forth in SEQ ID NO: 1,2,3,4,5,6,7, or 10;
   b) a nucleotide sequence selected from the group consisting of sequences deposited as ATCC Accession Nos. 207123, 207120, 207125, 207121, 207122, 207124, 207126, and 207119;
   c) a nucleotide sequence comprising at least 40 contiguous nucleotides of the sequence set forth in SEQ ID NO: 1, 2, 3, 4, 5, 6, 7, or 10; and
   d) a nucleotide sequence that has at least about 70% sequence identity to a sequence set forth in a) or b).

26. The plant of claim 25, wherein said plant is a monocot.

27. The plant of claim 26, wherein said monocot is maize.

28. The plant of claim 25, wherein said plant is a dicot.

29. A plant stably transformed with a DNA construct comprising a heterologous nucleotide sequence operably linked to a promoter that is capable of initiating transcription in a plant cell, wherein said promoter comprises a nucleotide sequence selected from the group consisting of:

a) a nucleotide sequence comprising the sequence set forth in SEQ ID NO: 8;
b) the nucleotide sequence deposited as ATCC Accession No. 207127;
c) a nucleotide sequence comprising at least 40 contiguous nucleotides of the C-terminal end of the sequence set forth in SEQ ID NO: 8, wherein said C-terminal end comprises nucleotides 272–467 of SEQ ID NO: 8; and
d) a nucleotide sequence that has at least about 70% sequence identity to a sequence set forth in a) or b).

30. A plant stably transformed with a DNA construct comprising a heterologous nucleotide sequence operably linked to a promoter that is capable of initiating transcription in a plant cell, wherein said promoter comprises a nucleotide sequence selected from the group consisting of:

a) a nucleotide sequence comprising the sequence set forth in SEQ ID NO: 9;
b) the nucleotide sequence deposited as ATCC Accession No. 207128;
c) a nucleotide sequence comprising at least 40 contiguous nucleotides of the C-terminal end of the sequence set forth in SEQ ID NO: 9, wherein said C-terminal end comprises nucleotides 86–467 of SEQ ID NO: 9; and
d) a nucleotide sequence that has at least about 70% sequence identity to a sequence set forth in a) or b).

31. Seed of the plant of any one of claims 25–30.

* * * * *

UNITED STATES PATENT AND TRADEMARK OFFICE
CERTIFICATE OF CORRECTION

PATENT NO. : 6,177,611 B1
DATED : January 23, 2001
INVENTOR(S) : Rice

Page 1 of 1

It is certified that error appears in the above-identified patent and that said Letters Patent is hereby corrected as shown below:

<u>Column 39, claim 13,</u>
Line 7, "297123" should read -- 207123 --.

<u>Column 40, claim 21,</u>
Line 8, "in" should read -- is --.

Signed and Sealed this

Twelfth Day of February, 2002

Attest:

JAMES E. ROGAN
*Attesting Officer*     *Director of the United States Patent and Trademark Office*

SEQUENCE LISTING

<160> NUMBER OF SEQ ID NOS: 34

<210> SEQ ID NO 1
<211> LENGTH: 1392
<212> TYPE: DNA
<213> ORGANISM: Zea mays
<220> FEATURE:
<223> OTHER INFORMATION: H2B histone promoter

<400> SEQUENCE: 1

```
cgacggcccg ggctggtatc gataaatgtt tccacataga ttttgcatat cataatgatg      60
tttgtcgttc cgtatctatg tttcatacaa aatttttacg catatcgcaa cacatgggca     120
catacctagt gactgtataa ctctgcatgt atgagtgtat gactatatga tgtagtaact     180
aataagaagg gtagacattt gagtgattct tttattcctg gacttgtaag acttgacatt     240
tctgccttga gtgcgataca tcatatggac aggggttatg catacactgc ttgtttgttg     300
tttatgttct aagagcatct ccaacaacgt gacatatgaa aatgccctac aatttaaaaa     360
tggttatatt ttataaaatt tagggcataa ataaaacatc ccgctccaac attaaagcct     420
taaatctatt atagggaagc ccactatgat atagtatatt tgaggcactt tagagggtgc     480
cctataattt tttgaccatt tttttatgaa atgagacact attggagtat ttttttttccg     540
tagagcacca tatttcaatt tgagacacca atttaaggca ttgttggaga tgttctaaat     600
gttggtttat tttgtctgta tcgttgtggt tttgatagtg gtgcctttgc aatgtacatc     660
ttacattgac aataataata ggtaaaactc tacaaatttt ttatctaatg gactcttgta     720
tgaaacattg tacttgcaca catctgatgt aaacactgca tacttttaac agtgacaaga     780
ttctgtttca ttttagggct agtttgggaa ccaaatttta ttagggtttt tattttctaa     840
gaaaagtaa tttatttttac cttgagaaaa tataaattac ttgagaaaat agagttccaa     900
actagctctt atctttgtcg aatcctcctc tattcaaatg tgacatttct ggcacgtgac     960
aactggtgat gttgtagact gtgttaagta atacgtgtca ttattactaa atgccatttt    1020
agtaaatgtt gagtatgtac tctactacag taagtattat tggtgtattt acactagaca    1080
gttggcggcc tggcgggtaa agttatcctg tagaaagttg ggccaggcca aaaccaaccg    1140
ccaaaggaaa ggccttccgg cccgcccacc tttgcgcgcc gaaggtcagt tccttcagtc    1200
tcctcccgct tcagactctg accacgtcga caatccgggc cgaaacacat ctgcaccgtc    1260
cacttgcgac agattgaaca caccacttct atccacgtca gcgatccgtg gcactagccc    1320
ttccaccaat cagcccaagt tgcccctttc ctttaaattc gccgcaccca ttgctcttct    1380
cacggccata ga                                                       1392
```

<210> SEQ ID NO 2
<211> LENGTH: 1300
<212> TYPE: DNA
<213> ORGANISM: Zea mays
<220> FEATURE:
<223> OTHER INFORMATION: met-1 promoter

<400> SEQUENCE: 2

```
gaatataggc aacaccccac actggtaggt aaagctccgg gattgtgact gagatgggga      60
tgatgacgtt gtagagaata caggcagccg tcggcgctac aactctcctc acaaagaaga     120
agctatagag catatagaac ttcttgacga gtgatatatc ctagcggaac aacaagtggg     180
gctaattttt agattttccc ctgcgaaagg catgatttgc cagaatggga acctgggcag     240
atatatgctc accttggcaa acaaaacatc ctttgccatc ttacggaata agtttgcacc     300
acctagacca ccggaattgc tgccgacagt aggccttgta agtggacggc agttcactct     360
tgacctgtaa atataacatg tttgcatagt caaatgatca catcaaatat atttaatttt     420
ggcaacactt ttatatgtca aaatctactc actctaacgt ctccaacata tacgaatttc     480
cagccctttta gtgttgctcg aaccgccaag tccatgcctt caactgtagt tcggtccttc     540
caacctcctg catctcttat ggctcctgta cgccacactc cagcagttcc tagaatagac     600
ataccatcag gaagaattta tggtcttgaa attgacattc tggggtggtt ccctctcttt     660
ggggaatttg tttgtactct ttagaggttt caaaagatgt gtaccgttga aactgaagaa     720
ggcaaaggtc gctgatcctg cttcttgttc aactttgaag tggtagtcgt aaaacatctt     780
ttgtacccctt gtcagcaggc ttgtcgtgtc attcactgca aaattctgtc aattaagaat     840
tggaccgatc agagtgaata aaaatactat atcgctcgag aagcttatgc actagcagtt     900
ctcttttca tgttatatca tctttgaaca gttctatgcc atctttctgg catcatcatt     960
aaagaatgtg aaaatatatt ttattgtcat cattatgaaa cgtgatgcct attttataag    1020
cccaaaacag tgaggttgtc tgttccaagt tccttgtgct atttgtaaga actatctgtg    1080
cacttctcac aagaaaaaca tctgaaaatg gagaaagtat tccattgtgg tggtatactg    1140
aaatgtggga gagcatatct gacaaatttg acatgaggtt taagaaatat ttcccatagt    1200
atttttctat tccataaatt aatcatgtgc atttgttata gacgggtagc tggaaaagtg    1260
tgctcaagaa ctagcaggga atggaccagc caggccgtcg                          1300
```

<210> SEQ ID NO 3
<211> LENGTH: 166
<212> TYPE: DNA
<213> ORGANISM: Zea mays
<220> FEATURE:
<223> OTHER INFORMATION: alpha-tubulin 3-18 promoter

<400> SEQUENCE: 3

```
cgacggcccg ggctggtcca acctccaagc ctacaaccag atcagccggt ctggtactgt      60
gcttctgtgg cacgaaaaaa ccgaccgttg cacggacgag aaacccgaac cgtcgaaaca     120
atcgtaatcc ccaggggctc aaacgcaaaa caccgtccgc tcccct                   166
```

<210> SEQ ID NO 4
<211> LENGTH: 1023
<212> TYPE: DNA
<213> ORGANISM: Zea mays
<220> FEATURE:
<223> OTHER INFORMATION: efla-11 promoter

```
<400> SEQUENCE: 4
tgttaacaag acgaatcaat gattagaaac actagtaaat taatactacc agtaacgaca      60
caatttatcg gatgggatca gaaactagat ctaacgttgt cgccggagtt atgagcttga     120
aaaaagcttg atacacataa gcagtgtaaa aataaagaag caaatattaa acagagcaat     180
caatgtaata taaaaaataa agcaggcata gaaaataaag gcaaactga taagcgtgcg      240
cacatgattt tgagccagta agacgaattc aaaattaggc acaacaactc tataaagcag     300
atcaggaatt tggtcatatt atgaggttac aactcttact gcgcatgaac tacaaagaca     360
agtatcggtc aaatagaaac tacagcagct ctacacctca aaaattcgat ctgactttat     420
taagaccacg taacacgacc gcaagcgcaa ttaagaagtc gtccaactac ggtggcacgg     480
tgcgtatgta atttatcaaa tccagaagca actatccgta agaatcaggt catccaaaca     540
cggaagcaaa caaaaccaca aaaactaaga gaatggagac gcagtagcta caattaatcg     600
caaacagaag gccgaatcac ttcaggcacg gggaggcaac agagcacagc tttgaaccac     660
tgcctatctc atcgagcacc tcaaggacaa agatcgagcg acagaggatt agctaccttg     720
caagggacag aggccgaaat ggaggcgcac aaggcagacg gcgagttggg gaggaaggtg     780
ctggcctcta gggttcggga ctttatataa gggtgtcgga gtggccggac cagcccaata     840
cttgacttcc gaatggcggc ccagggccca taaacgagc gagacatagt atatgggatg      900
actgaatgac aatgttattt gctcttaata ttgtatggca gcacttttag gtatatgccc     960
caatttctct aatactctac tctttcatat tctaatggca tctcatgtta tgttggccta    1020
aat                                                                  1023

<210> SEQ ID NO 5
<211> LENGTH: 1022
<212> TYPE: DNA
<213> ORGANISM: Zea mays
<220> FEATURE:
<223> OTHER INFORMATION: efla-15 promoter

<400> SEQUENCE: 5
gttaacaaga cgaatcaacg attagaaaca ctagtaaata ttaatactac cagtaacgac      60
acaatttatc agatgggatc agaaactaga tctaacgttg tcaccggagt tatgagcttg     120
aaaaaagctt gatacacata agcagtgtaa aaataaagaa gcaaatatta acagagcaa      180
tcaatgtaat ataaaaaaat aaagcaggca tagaaaataa agagcaaact aataagtgtg     240
cgcacataat tttgagccag taagacgaat tcaaaattag gcacaacaac tctataaagc     300
agatcaggaa tttggtcata ttatgaggtt acaactctta ctgcgcatga actacaaaga     360
caagtatcgg tcaaatagaa actacagcag ctctacacct caaaaattcg atctgactt      420
attaagacca cgtagcacga ccgcaagcgc aattaagaag tcgtccaact acggtggcac     480
ggtgcgtatg taatttatca aatccagaag caactatccg taagaatcag gtcatccaaa     540
cacggaagca acaaaaccaa aaaaaacta agagaatgga gacgcagtag ctacaattaa      600
tcgcaaacag aagaccgaat cacttcaggc acggggaggc aacagagcac agctttgaac     660
cactgcctat ctcatcgagc acctcaagga caaagatcga gcgacagagg attagctacc     720
ttgcaaggga cagaggccga atggaggcg cagaaggcag acggcgagtt ggggaggaag      780
gtgcttgcct ctagggttcg ggactttata agggtgtc ggtgtggccg gaccagccca       840
atgtgacttc cgatttccga atggcggccc agggccataa acgagcgag acagggtgtg      900
tttggttcgg ttttttttctg accagcttat atgaaaagct ggttgtgggg aaaagctggc    960
```

```
tgttgggaaa aactggtggc taaaatttag gtgtttggtt cgccagacca gcccgggccg   1020
tc                                                                  1022
```

<210> SEQ ID NO 6
<211> LENGTH: 1769
<212> TYPE: DNA
<213> ORGANISM: Zea mays
<220> FEATURE:
<223> OTHER INFORMATION: efla-16 promoter

<400> SEQUENCE: 6

```
cgacggcccg ggctggtctg acttcagtgt aattcaaagc cggaacagat aaaagtgtgt     60
cttgccgat gatgttaaat agagtaatac ctgattattg ctgtcaagtg gttgtgttag    120
taattggaat actgttggag tatgtttccc tttatctttc cattttatca tctgtcagtg   180
ctcgtgactt tatggtctct aaatttctta gatagttcat gtcgtaccat gaatgtgtg    240
tctgtaacat tggtcaacca tattgttcat gtcttcaact ctatttcgaa gtcacaaact   300
gatcacttgg agtttcggac gtgaagcaac gacaggcatc aatgcctact tcatatataa   360
aactgcttgc ttgttgcatg ctgttacagc acctaagacc taagtacata cttgcttcct   420
tttcttattt gtatgctggg tcccatggac cccgttttgt tttgggtttc cctacacatt   480
gtccccggac ttacagatga caaatatgat gtgttctatg agtcacgtcg aaagaaagaa   540
atgtacttta gcatttcact gtacataagt ccatcgattt cacattatac tcttctacct   600
aacaaagccc aaaattgagc tacacatctt tttgatatta gtacgttaat gttagtcaat   660
tgttatcagg cagcgatgtc tgattataga tctcaaagta agactgtcat ttccccttag   720
ttcagttagt atagttgctt aaattcagca agtctgaata cttcaacaag gcacaataag   780
ggaggttcag cacgtaagtt agtataggac catgtgtaat ctatttaaca gagaaaatag   840
gcataaaaac gactagcctg cagtcgtgcg gatatttgaa tataagtgtt cagatgggcg   900
agcgcccttg tgctttctct attcgctaaa attcttgaaa agcatgtaag cttttcgcaa   960
ggttcgttag cagtgactac ctgtttgtag tacatgaaca ttagtatttt acttccctca  1020
gttcaccttt cttgtgcttg caatacaata cattattttt tacggtgaat ttataaacca  1080
tatttggtaa gttatatttta tactagccta atgcactcga ctcttctatt tagattaagt  1140
ttggtgaata atttatatgt ttgtgtagcg aaagactcat atttatttag tttttttctt  1200
gtcaaggata ggacataatt tggtgctttg cttgtgtaat tatgtctacg cacttaaaaa  1260
atggcacttt ccttacgcct tggtacagtg cttcaataat gagtggataa atgtttatg   1320
aagttgatct tattttttg agaattcagc attaataatc atgcgccaca ttatccaaag   1380
cttatggtat tctttatatg attttagtgc taataatgtt gtgccactac agggcggtgc   1440
cggctctgat ctggtttata aagtagcaaa ttttgaattt gttttgttgg ctctaaattc  1500
tgtgtgaaca cttattagtc tgctctgttt attctttagt gcttcttata ttatattgtt  1560
tgctctattg aatgtttcta ggtctgcttt atcccttgct aacatgtacc atgctttttc  1620
taagctgatt acagtagttg caactccaaa tttagtttct aattccatct aataattttt  1680
tttgttagtg gctttagtat tgtgtgattt ttacttgcgt tcctaataat ttattcgttt  1740
gattaacagt ttaagcttca cggatccac                                    1769
```

<210> SEQ ID NO 7
<211> LENGTH: 461
<212> TYPE: DNA

<213> ORGANISM: Zea mays
<220> FEATURE:
<223> OTHER INFORMATION: rps8 promoter
<220> FEATURE:
<221> NAME/KEY: unsure
<222> LOCATION: (459)
<223> OTHER INFORMATION: Nucleotide at this position may be a or
     g or c or t.

<400> SEQUENCE: 7

```
ggtacagaag tgagagaagg aaaccctagg tatcgagtgt gtatatagga ggagggaagg      60
tggggcgcct gggccgcata aaatgtggaa aggctctgaa ccgacaaatt tggatgttta     120
acagacctgt aaatggttct gtactctaaa atatagtata tagagaatac atgcatcttt     180
ttatctccaa caaaagtctg taaagaatca tctaaagttt agagcacggc atgcatccgc     240
taaaaatgaa gggcgtacgg ttctactcta tacactgtgc ttatttattg tgtttgctca     300
ttcacatgca catgaccggt aaaaatcaat atagaatgtg aaatatggta cactattgat     360
atagaggatg aaatttagag gacattgctg gagatggaga aaatatagag aacaaaattt     420
tttagagagt gctgtaaagg actgagaata ttctttttang g                       461
```

<210> SEQ ID NO 8
<211> LENGTH: 467
<212> TYPE: DNA
<213> ORGANISM: Zea mays
<220> FEATURE:
<223> OTHER INFORMATION: cab-10 promoter
<220> FEATURE:
<221> NAME/KEY: unsure
<222> LOCATION: (370)
<223> OTHER INFORMATION: Nucleotide  at this postion may be a or
     g or c or t.

<400> SEQUENCE: 8

```
gtagcgagac ttgcagatcg atggtggctt gaggtgctgt ggacttgtgg aggcgacgaa      60
ggtatttaaa gcgacggagg gaaacaccgc cgcgagcaag ttctatcttg aatgttgcca     120
gaaaataaaa aataaatctg atgcttggat gccattggtg cgtccgggat gctgaacac      180 ttggcgcgac gggagcctca gggggacgat gaggcagatg tgggctgtgg ctgaggctag     240
gaatctccgt ggagaagggt gattgggcgc cgtaaatact actatatacc tttgttccaa     300
gatgtctgtt ttaacttctc taactttaac tgagttcata taaaaaatcc aaacatatta     360
atcaacttan ttataaattt gcctaaattt aaataagctc tacttacgac aaaaccatat     420
taaacgtttt aaaacgtcca caaccccccaa ttttgcaatg caaaagg                  467
```

<210> SEQ ID NO 9
<211> LENGTH: 467
<212> TYPE: DNA
<213> ORGANISM: Zea mays
<220> FEATURE:
<223> OTHER INFORMATION: cab-20 promoter
<220> FEATURE:
<221> NAME/KEY: unsure
<222> LOCATION: (460)
<223> OTHER INFORMATION: Nucleotide at this position may be a or
     g or c or t.

<400> SEQUENCE: 9

```
gtagcgagac ttgcagatcg atggtggctt gagatgctgt ggacttgtgg aggcgacgaa      60
ggtatttaaa gcgacggagg gaaacctaca atacggagta tgagctaatc taggcggcat     120
ctcccagtca ccttgatggt gccaatgaat aattatttag ttcgttttat tgttatcatt     180
```

```
tattttttgta agactcttcc actatgtaat aatgattatg acatttatct ctatacactt    240
tgtcattata tgtgatgttc tcctttggcg cacatatgag acgcacccgt ctttatccct    300
taaatttggg tgtgacactc cgaaagcccT atacaatcac tataaaatct gccaagacct    360
gggatttgat tgttgtcctc agctcgaaag tgacattgta cccagggaat tcggctgccc    420
atttggctat tctggcagat gccttgagaa ttctaaatan gtctccc                  467

<210> SEQ ID NO 10
<211> LENGTH: 565
<212> TYPE: DNA
<213> ORGANISM: Zea mays
<220> FEATURE:
<223> OTHER INFORMATION: gpc4 promoter

<400> SEQUENCE: 10
taacagtacc aacttgcaca tcagaagccc cgcgagcaca gaagtgtata gaacatatgg     60
atctgctagc aagtattcct taagaagtat ttctgcttta tacttatagg ccttagctgc    120
catgattggg tcaacaggaa aatccataat ctgatccatc aagtcaacag tcagattgtt    180
gaacagagtg gttccattcc ccacaatcca taagcaatgc ctacaacaaa ttgttaaaaa    240
ttaaatagtt ttattatcat gcaccagata aagattatg aagtaattga agtgaaattt     300
aaatgcttgg cgcagaactt acttggcccc tgttaacaat atatagtata gatatgtgct    360
cgtgcgttgc gatggaagta aaaaatttgt atgaaacatt gatacggaac gacaaaaatc    420
actataatat gcaaaatata cgtggaaaat attatcaata tcacacaaat taattctaaa    480
aagttaattt agaattttta attacagaca aatatgtcga caactaatca gctaatcctt    540
tttagcgata ccagcccggg ccgtc                                          565

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      PCR Primer

<400> SEQUENCE: 11
gtaatacgac tcactatagg gc                                              22

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 12
cgcgggctcc tcctccgccg gcttctt                                         27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 13
gtacttcttg ccgcacttgc agcttga                                         27
```

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Maize gene-specific PCR primer

<400> SEQUENCE: 14
ggtcttgtca ccgggcatct gaccatc                27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Maize gene-specific PCR primer

<400> SEQUENCE: 15
gtcctgtggt ggtcgacttg ccagagt                27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Maize gene-specific PCR primer

<400> SEQUENCE: 16
ttcttcctcc aggccttctg ctttcca                27

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Maize gene-specific PCR primer

<400> SEQUENCE: 17
aggagacgac gacggcacgt tcacggc                27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Maize gene-specific PCR primer

<400> SEQUENCE: 18
taatcggtgc tgatgaaggg gtcgttc                27

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Maize gene-specific PCR primer

<400> SEQUENCE: 19
actatagggc acgcgtggt                 19

```
<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 20
gggcttcttc tcggccttgg gcgccat                                27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 21
agccgcagct tgatccgcag ttgcaag                                27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 22
cccagcacgc gtttccgacc tggatac                                27

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 23
tggccaataa ccacaatgtt gatgtg                                 26

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 24
cgcttgtgca tcgagtcacg cgagata                                27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 25
gaaggctgtg gaggagaggg ccatggt                                27

<210> SEQ ID NO 26
<211> LENGTH: 24
```

```
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 26
acccattgat cccgatcttg atct                                           24

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 27
gaccatggtg tcgtgtggat ccgatgcggc tgct                                34

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 28
gaccatggtg tcgtgtggat ccccttgtgg tgc                                 33

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 29
gaccatggtg tcgtgtggat ccggtgttgt tgaacg                              36

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 30
gaccatggtg tcgtgtggat ccgtgagatt gaac                                34

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 31
gaccatggtg tcgtcgtgtg gatccgtgaa gcttaa                              36

<210> SEQ ID NO 32
<211> LENGTH: 36
<212> TYPE: DNA
```

-continued

```
<213> ORGANISM: Artificial Sequence
<220> FEATURE:
<223> OTHER INFORMATION: Description of Artificial Sequence: Maize
      gene-specific PCR primer

<400> SEQUENCE: 32
gaccatggtg tcgtgtggat ccgcctgctc cttgtc                              36

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Maize
      gene-specific PCR Primer

<400> SEQUENCE: 33
gaccatggtg tcgtgtggat cctgcactgc tac                                 33

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 34
gaccatggtg tcgtgtggat ccacaaacac aagc                                34
```